United States Patent
Niles et al.

(10) Patent No.: US 7,036,500 B2
(45) Date of Patent: May 2, 2006

(54) NEBULIZER WITH AUXILIARY INLET PORT

(75) Inventors: Rex A. Niles, Oneida, NY (US);
Richard K. Pelerossi, Rome, NY (US);
Fredrick M. Richards, Clinton, NY (US)

(73) Assignee: Smiths Medical ASD, Inc., Keene, NH (US)

( * ) Notice: Subject to any disclaimer, the term of this patent is extended or adjusted under 35 U.S.C. 154(b) by 0 days.

(21) Appl. No.: 10/828,972

(22) Filed: Apr. 21, 2004

(65) Prior Publication Data

US 2005/0235985 A1    Oct. 27, 2005

(51) Int. Cl.
*A61M 11/00* (2006.01)
*A61M 16/00* (2006.01)

(52) U.S. Cl. ............... 128/200.14; 128/200.11; 128/203.12

(58) Field of Classification Search ........... 128/200.14, 128/200.21, 203.12, 204.14, 200.11, 202.27; 239/338
See application file for complete search history.

(56) References Cited

U.S. PATENT DOCUMENTS

| | | | |
|---|---|---|---|
| 3,353,536 A * | 11/1967 | Bird et al. ............. | 128/200.18 |
| 4,792,097 A * | 12/1988 | Kremer et al. ............... | 239/338 |
| 4,805,609 A | 2/1989 | Roberts et al. | |
| 4,827,921 A | 5/1989 | Rugheimer | |
| 4,951,661 A | 8/1990 | Sladek | |
| 5,119,807 A * | 6/1992 | Roberts et al. ......... | 128/200.24 |
| 5,277,175 A | 1/1994 | Riggs et al. | |
| 5,570,682 A | 11/1996 | Johnson | |
| 5,823,179 A * | 10/1998 | Grychowski et al. .. | 128/200.18 |
| 6,041,776 A | 3/2000 | Briggs, III | |
| 6,328,030 B1 * | 12/2001 | Kidwell et al. ......... | 128/200.21 |

* cited by examiner

Primary Examiner—Mital Patel
(74) Attorney, Agent, or Firm—Luedeka, Neely & Graham, P.C.; August E. Roehrig, Jr.

(57) ABSTRACT

A nebulizer having a supplemental gas inlet port carried by the nebulizer head at a position removed from the nebulizer chamber so that the supplemental gas introduced does not entrain the liquid medicant effecting the rate of medication application to a user.

10 Claims, 1 Drawing Sheet

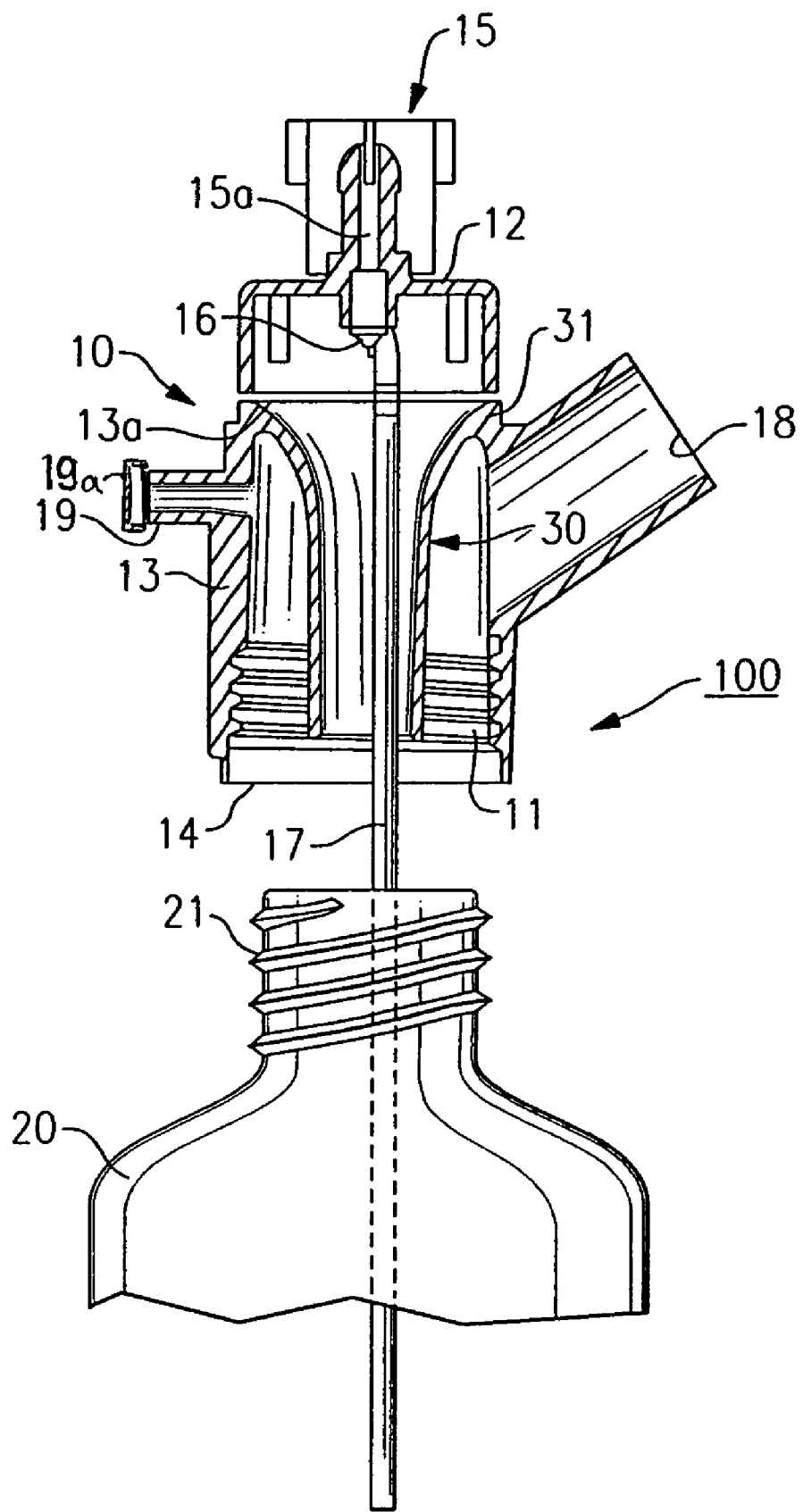

NEBULIZER WITH AUXILIARY INLET PORT

FIELD OF THE INVENTION

This invention relates in general to an improved nebulizer and, in particular, to an improved nebulizer wherein an auxiliary gas port is carried by the nebulizer head in a position removed from the nebulization chamber to introduce an auxiliary gas into the nebulizer head, when desired, without effecting the rate at which medication is applied to the nebulizer user.

BACKGROUND OF THE INVENTION

Persons requiring treatment of certain kinds of respiratory conditions frequently need to have medications delivered directly to the lungs. Nebulized or aerosolized solutions are the preferred method of delivery of respiratory medication because the medicant is fragmented into small particles that are more efficiently deposited near sites of drug activity in the lungs.

While nebulizers are well known to those skilled in the art, aerosolization of medications in a nebulizer is effected by putting a liquefied medication into a container or liquid reservoir and introducing a pressurized flow of gas through an aerosol nozzle carried within a nebulization chamber which is coupled to the liquefied medication contained in the liquid reservoir by a liquid draw tube. As the pressurized high velocity gas flows through the aerosol nozzle, the liquefied medication is drawn through the liquid draw or aspirator tube into the path of the high velocity gas and is fractured thereby into a mist, becoming entrained with the gas flow out of the nebulization chamber through the container and out therefrom through an output port.

In certain applications, nebulization therapy can be enhanced through the use of an auxiliary gas to supplement the nebulizing or driving gas being introduced through the aerosol nozzle. Such supplemental gases may be oxygen, helium or a combination of these two gases, referred to as heli-ox. The use of helium, an inert and metabolically stable gas which readily diffuses into swollen airways or heli-ox as a supplement to the nebulizing gas is known, and frequently used to drive the nebulized medication deeper into a user's lungs to deliver medications to bypass obstructed airways for a greater and more rapid effect from the medication.

One of the problems encountered when using supplemental gases, however, is that the injection of the supplemental gas into the nebulizing gas or into the nebulizing chamber effects the rate at which the liquefied medication is fractured or passes out from the container through the aerosol output port. Generally, the rate at which the liquefied medication is to be nebulized and delivered to the user, is determined based upon, among other factors, the rate of flow and density of the driving or nebulizing gas being introduced into the nebulization chamber. When a supplemental gas is introduced into the nebulizing gas flow or into the nebulization chamber, the total quantity of medication delivered through the nebulization chamber changes. Accordingly, the predetermined rate at which the liquefied medication is discharged through the aerosol output port varies from that at which it was initially set.

SUMMARY OF THE INVENTION

The present invention is directed to overcoming one or more of the problems or disadvantages associated with the relevant technology. As will be more readily understood and fully appreciated from the following detailed descriptions of a preferred embodiment of the present invention, the invention is embodied in an improved nebulizer wherein a supplemental gas may be introduced into the nebulizer head at a position after the liquefied medication has been fractured or nebulized, so that the introduction of the supplemental gas does not effect the rate at which the nebulized liquefied medication is applied to the user.

DESCRIPTION OF THE DRAWINGS

Further objectives of the invention, together with additional features contributing thereto and advantages accruing therefrom, will be apparent from the following description of a preferred embodiment of the invention which is shown in the accompanying drawing, wherein there is illustrated an elevational view of the invention with portions broken away to better illustrate the internal construction thereof.

DETAILED DESCRIPTION OF A PREFERRED EMBODIMENT

Referring now to the drawing, there is illustrated a preferred embodiment of the improved nebulizer 100 which is preferably molded from translucent plastic and includes a nebulizer head 10 which is adapted to be received on a liquid container or receptacle 20. To this end, the lowermost portion of the nebulizer head 10 is open and formed with an internal thread 11 which is sized to receive a complementary external thread 21 formed on the top or neck portion of the liquid receptacle 20 for forming a liquid-tight seal.

The nebulizing head 10 has a closed circular-shaped top 12 and a depending skirt 13 forming a generally cylindrical shape with an open bottom 14 adapted to receive the liquid container 20. A nebulization chamber 30 is formed inside the nebulization head 10 and spaced downwardly from the top 12. The nebulization chamber 30 extends downwardly from a point of attachment 31 on the inner wall 13*a* of the skirt 13 towards the open end 14 of the nebulizer head, forming a chamber in which the liquid contained in the liquid container 20 is entrained in a driving or nebulizing gas introduced through the top 12 of the nebulizer head 10 into the nebulization chamber 30.

The top 12 of the nebulizer head 10 supports an adapter 15 by which a suitable source of driving or nebulizing gas (not shown) is connected such as by tubing for introduction into the nebulizing chamber 30. A conventional nebulizing nozzle 16 is supported within the nebulizing chamber 30 beneath the top 12, and is coupled to a passageway 15*a* formed through the adapter 15 through which the driving or nebulizing gas is introduced into the nebulizing chamber 30. The nebulizing nozzle 16 communicates with a suitable orifice at an upper terminal end of an aspirator tube 17 which extends downwardly into the liquid medicant contained in the liquid receptacle 20. In this manner, when a source of driving or nebulizing gas is coupled to the adapter 15, and introduced to the nebulizing nozzle 16, the liquid medicant contained within the receptacle 20 will be entrained in the driving or nebulizing gas and discharged out from the nebulizer chamber 30. The entrained aerosol so formed will then pass through the nebulizing head 10 to be discharged from the nebulizer 100 through a nebulized aerosol discharge outlet 18 formed through the sidewall 13.

To provide for the introduction of a supplemental gas into the nebulizer 100, an auxiliary gas inlet port 19 is formed in the side wall 13 at a point preferably opposite to the nebulized aerosol discharge outlet 18. The auxiliary gas inlet port extends into the nebulizing head 10, but not into the nebulizer chamber 30, so that the supplemental gas introduced through inlet port 19 will not effect the rate at which the aerosolized medicant is delivered from port 18. As heretofore described, when a supplemental gas is introduced into the driving or nebulizing gas, or the nebulizing chamber 30, the supplemental gas so introduced effects the uniformity of the administration of the medication. When a supplemental gas is so introduced, the rate of medication application increases with the increased gas flow. By introducing the supplemental gas through the auxiliary gas inlet port 19, the supplemental gas does not change the rate at which medication exiting the nebulizer through port 18 is applied to the nebulizer user. When a source of supplemental gas is not being introduced through auxiliary gas inlet port 19, a conventional cap, not shown, may be placed over the external opening thereto.

While this invention has been described in the specification and illustrated in the drawing with reference to a preferred embodiment, the structure of which has been disclosed herein, it will be understood by those skilled in the art to which this invention pertains that various changes may be made and equivalents may be substituted for elements of the invention without departing from the scope of the claims. Therefore, it is intended that the invention not be limited to the particular embodiment disclosed in the specification and shown in the drawing as the best mode presently known by the inventors for carrying out this invention, nor confined to the details set forth, but that the invention will include all embodiments, modifications and changes as may come within the scope of the following claims:

What is claimed is:

1. A nebulizer head having an auxiliary gas inlet port for introducing a supplemental gas, comprising:
    a first chamber having a closed top, enclosing sides and an open bottom adapted to receive for coupling thereto a receptacle adapted to contain a liquid medicant to be dispensed at a predetermined rate of concentration;
    a second nebulizing chamber carried within said first chamber at a position spaced from said closed top and extending downwardly therefrom;
    said nebulizing chamber having an open bottom adapted to pass outwardly there through entrained and nebulized liquid medicant;
    a nebulizing nozzle in fluid communication with said nebulizing chamber for creating a nebulized aerosol from liquid medicant coupled thereto;
    means for coupling a flow of nebulizing gas into said first chamber to said nebulizing nozzle and through said second nebulizing chamber carried within said first chamber;
    an aspirator tube having a first end positioned in fluid communication adjacent to said nebulizing nozzle, and a second end positioned to be received into liquid medicant contained within the receptacle;
    an auxiliary gas inlet port for introducing a supplemental gas into said first chamber;
    said auxiliary gas inlet port having a discharge outlet in fluid communication with said first chamber at a position removed from the interior of said nebulizing chamber; and
    said first chamber having a discharge outlet spaced from said open bottom of said nebulizing chamber and said auxiliary gas inlet port for discharging liquid medicant entrained in said nebulizing chamber and the supplemental gas introduced into said first chamber through said auxiliary gas inlet port.

2. The nebulizer head of claim 1 wherein said auxiliary gas inlet port and said discharge outlet are in opposed positions relative to each other, and said nebulizing chamber carried within said first chamber extends there between.

3. The nebulizer head of claim 1 further including a receptacle for containing liquid medicant to be dispensed through said discharge outlet.

4. The nebulizer head of claim 3 wherein said receptacle includes means for releasably connecting said receptacle to said first chamber in sealing engagement therewith.

5. The nebulizer head of claim 1 wherein said nebulizing chamber has an open top attached to the interior of said first chamber at a position above said auxiliary gas inlet port and said nebulizing chamber extends downwardly therefrom such that said open bottom of said nebulizing chamber is positioned at a location removed from said auxiliary gas inlet port.

6. The nebulizer head of claim 5 wherein said nebulizing nozzle is supported from said first chamber top above said nebulizing chamber for entraining liquid medicant communicated thereto through said aspirator tube.

7. The nebulizer head of claim 6 wherein said nebulizing chamber extends downwardly within said first chamber such that said open bottom of said nebulizing chamber is positioned at a location below said auxiliary gas inlet port and below said first chamber discharge outlet.

8. The nebulizer head of claim 1 wherein said means for coupling a flow of nebulizing gas into said first chamber comprises an adapter for releasably coupling a source of driving gas to said nebulizing nozzle.

9. The nebulizer head of claim 1 wherein said auxiliary gas inlet port includes means for selectively closing said auxiliary gas inlet port when not in use.

10. A method of selectively introducing a supplemental gas into a nebulizer without effecting the rate of medicant application created in a nebulizer chamber by the entrainment of the medicant due to the action of a driving gas fracturing the medicant, comprising:
    passing a flow of driving gas into a nebulizer chamber of a nebulizer for fracturing medicant contained therein and creating a medicant aerosol in said nebulizer chamber;
    introducing a supplemental gas into said nebulizer at a location removed from said nebulizer chamber thereby mixing said supplemental gas with said medicant aerosol from said nebulizer chamber, without effecting the rate of medicant delivered from said nebulizing chamber to a nebulizer user; and
    discharging said mixture of said medicant aerosolized by said driving gas in said nebulizer chamber, and said supplemental gas, from said nebulizer.

* * * * *